(12) United States Patent
Jingu

(10) Patent No.: US 9,885,670 B2
(45) Date of Patent: Feb. 6, 2018

(54) INSPECTION APPARATUS AND ADJUSTING METHOD

(71) Applicant: Hitachi High-Technologies Corporation, Minato-ku, Tokyo (JP)

(72) Inventor: Takahiro Jingu, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 97 days.

(21) Appl. No.: 14/758,054

(22) PCT Filed: Dec. 19, 2013

(86) PCT No.: PCT/JP2013/084156
§ 371 (c)(1),
(2) Date: Jun. 26, 2015

(87) PCT Pub. No.: WO2014/109205
PCT Pub. Date: Jul. 17, 2014

(65) Prior Publication Data
US 2015/0346112 A1 Dec. 3, 2015

(30) Foreign Application Priority Data
Jan. 11, 2013 (JP) .................................. 2013-003961

(51) Int. Cl.
*G01N 21/93* (2006.01)
*G01N 21/956* (2006.01)
*G01N 21/95* (2006.01)

(52) U.S. Cl.
CPC ....... *G01N 21/9501* (2013.01); *G01N 21/956* (2013.01); *G01N 21/93* (2013.01); *G01N 2201/127* (2013.01)

(58) Field of Classification Search
USPC .... 356/237.1–241.6, 242.1–243.8, 426–431, 356/600–640
See application file for complete search history.

(56) References Cited

U.S. PATENT DOCUMENTS 5,133,602 A * 7/1992 Batchelder ......... G01N 15/0205
356/364
6,628,381 B1 * 9/2003 Komem ............. G01N 21/9501
356/237.4

(Continued)

FOREIGN PATENT DOCUMENTS

JP 10-325807 A 12/1998
JP 2004-177284 A 6/2004

(Continued)

OTHER PUBLICATIONS

Japanese Office Action issued in counterpart Japanese Application No. 2014-556361 dated Mar. 1, 2016 with English-language translation (fourteen (14) pages).

(Continued)

*Primary Examiner* — Tri Ton
*Assistant Examiner* — Jarreas C Underwood
(74) *Attorney, Agent, or Firm* — Crowell & Moring LLP

(57) ABSTRACT

An inspection apparatus which can be accurately calibrated regardless of a use environment or an amount of use time is implemented. A reference substrate 100 provided with a diffraction grating 107 is mounted on a transport system 110, an illumination region 106 is formed on the diffraction grating 107 by light 105 from an illumination optical system 104, reflected light is collected by a detection optical system 108, and an output value from a sensor 111 is measured. It is determined whether or not a difference between a simulation value preserved in a processing section 112 and the output value from the sensor 111 is within a predetermined allowable range, and the optical system is adjusted so that the difference enters the allowable range. Since standard data for performing calibration on the inspection apparatus is obtained by using the diffraction grating, it is possible to implement the inspection apparatus which can be accurately (Continued)

calibrated regardless of a use environment or an amount of use time.

36 Claims, 8 Drawing Sheets

(56) References Cited

U.S. PATENT DOCUMENTS

| | | | | |
|---|---|---|---|---|
| 6,781,688 | B2* | 8/2004 | Kren | G01N 21/9501 356/237.1 |
| 8,390,780 | B2* | 3/2013 | Makinouchi | G01D 5/38 355/53 |
| 8,547,545 | B2* | 10/2013 | Sasazawa | G01N 21/8851 356/237.1 |
| 8,681,328 | B2* | 3/2014 | Taniguchi | G01N 21/21 356/237.2 |
| 2006/0124874 | A1* | 6/2006 | Uto | G01N 21/9501 250/559.45 |
| 2008/0117437 | A1* | 5/2008 | Vuong | G01B 11/24 356/601 |
| 2011/0249112 | A1* | 10/2011 | Endo | G01N 21/956 348/92 |
| 2011/0286001 | A1 | 11/2011 | Taniguchi et al. | |
| 2013/0188184 | A1* | 7/2013 | Taniguchi | G01N 21/956 356/364 |

FOREIGN PATENT DOCUMENTS

| | | |
|---|---|---|
| JP | 2004-184322 A | 7/2004 |
| JP | 2008-58239 A | 3/2008 |
| JP | 2008-129017 A | 6/2008 |
| JP | 2010-85135 A | 4/2010 |
| JP | 2011-75431 A | 4/2011 |
| JP | 2011-232354 A | 11/2011 |
| JP | 2012-47654 A | 3/2012 |
| JP | 2012-154946 A | 8/2012 |
| WO | WO 2010/050488 A1 | 5/2010 |
| WO | WO 2010/084884 A1 | 7/2010 |

OTHER PUBLICATIONS

Notification of Transmittal of Translation of the International Preliminary Report on Patentability (PCT/IB/338) dated Jul. 23, 2015, and English translation of Written Opinion (PCT/ISA/237) dated Feb. 25, 2014 (eight (8) pages).

International Search Report (PCT/ISA/210) dated Feb. 25, 2014, with English translation (five (5) pages).

Japanese-language Written Opinion (PCT/ISA/237) dated Feb. 25, 2014 (four (4) pages).

* cited by examiner

[Fig. 1]
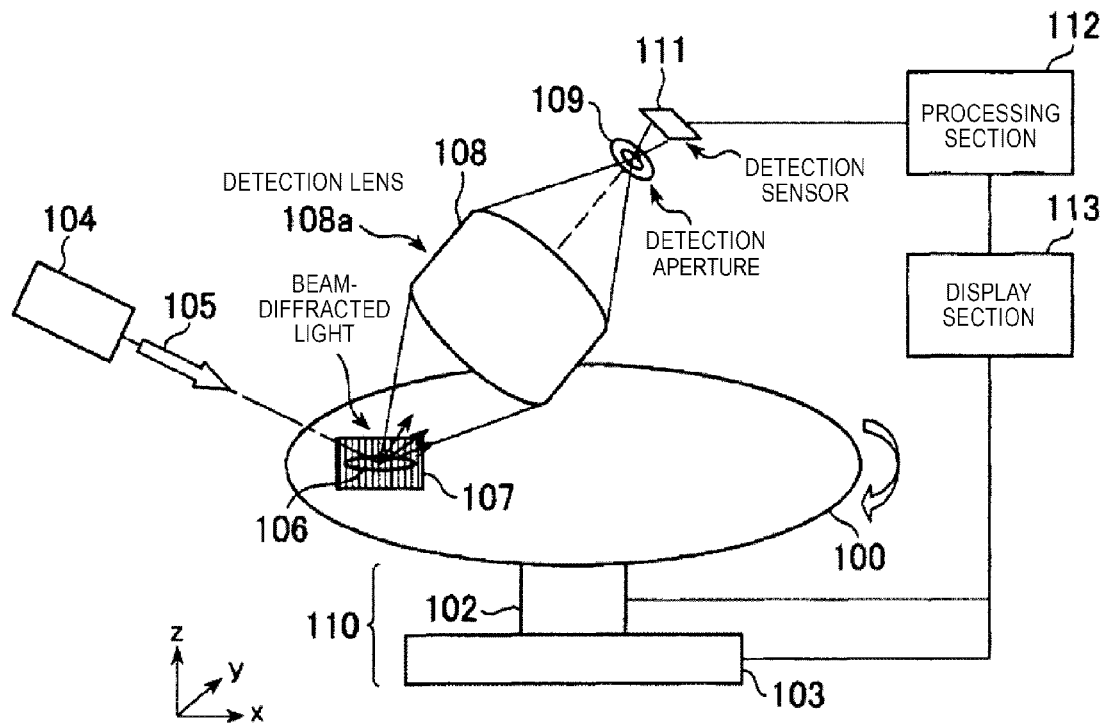
[Fig. 2A]
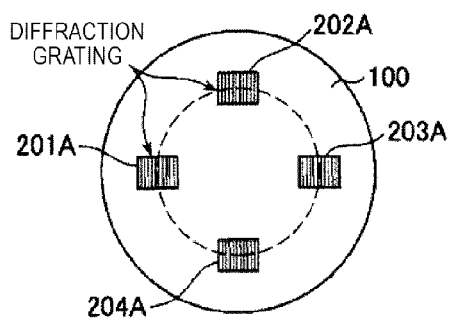
[Fig. 2C]
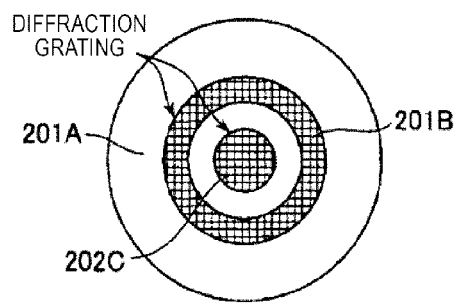
[Fig. 2B]
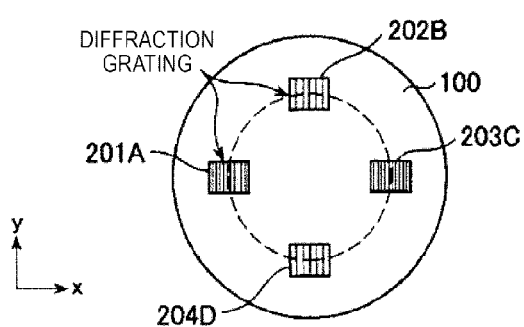

[Fig. 3A]
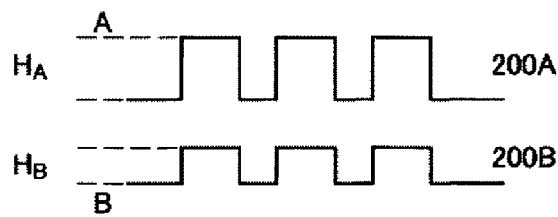
[Fig. 3B]
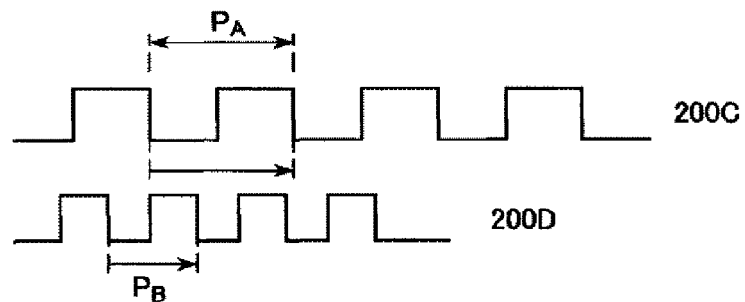
[Fig. 4A]
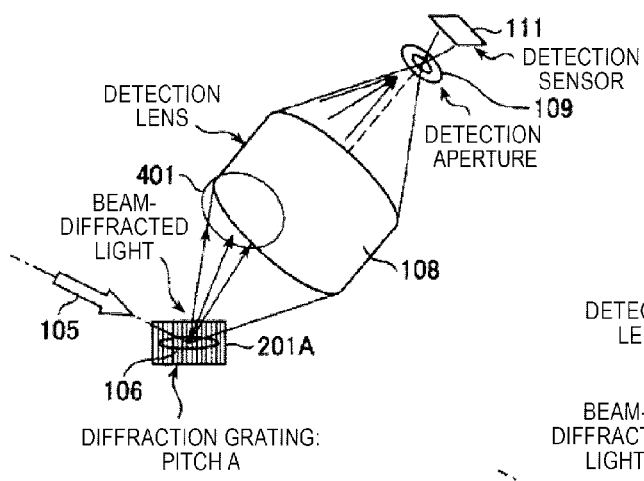
[Fig. 4B]
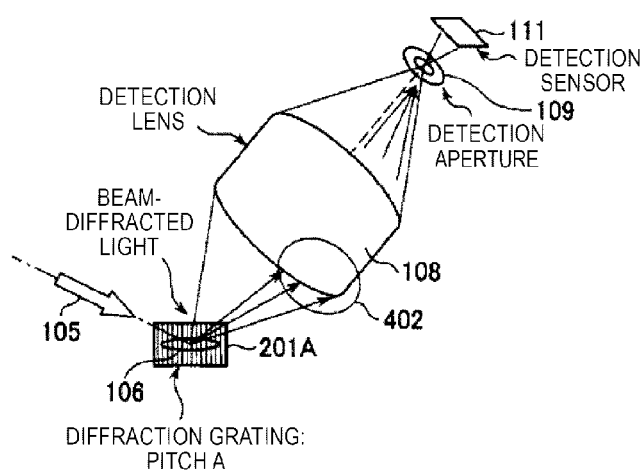

[Fig. 5]
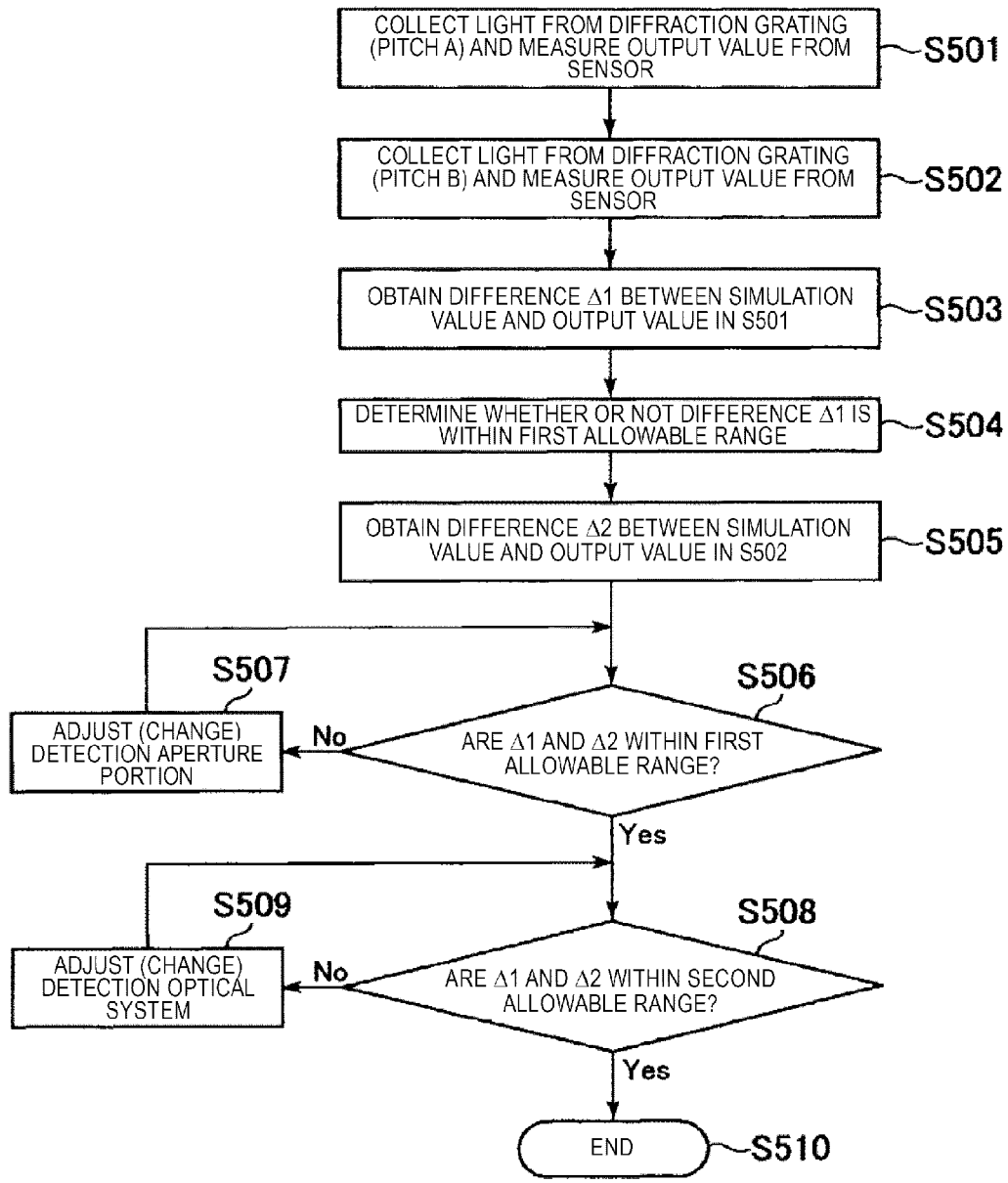
[Fig. 6]
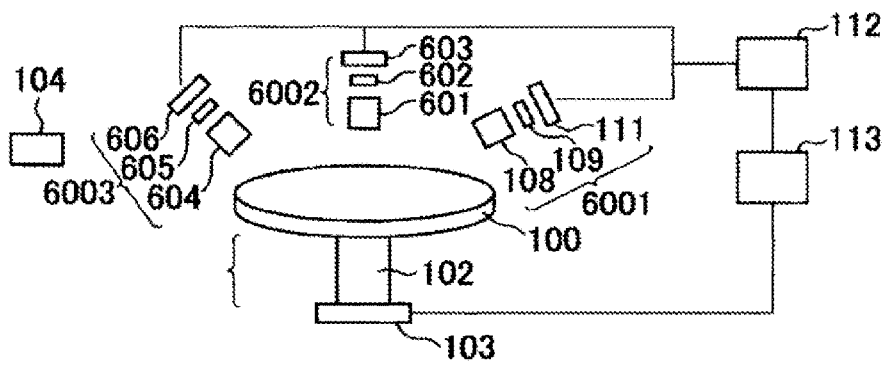

[Fig. 7]
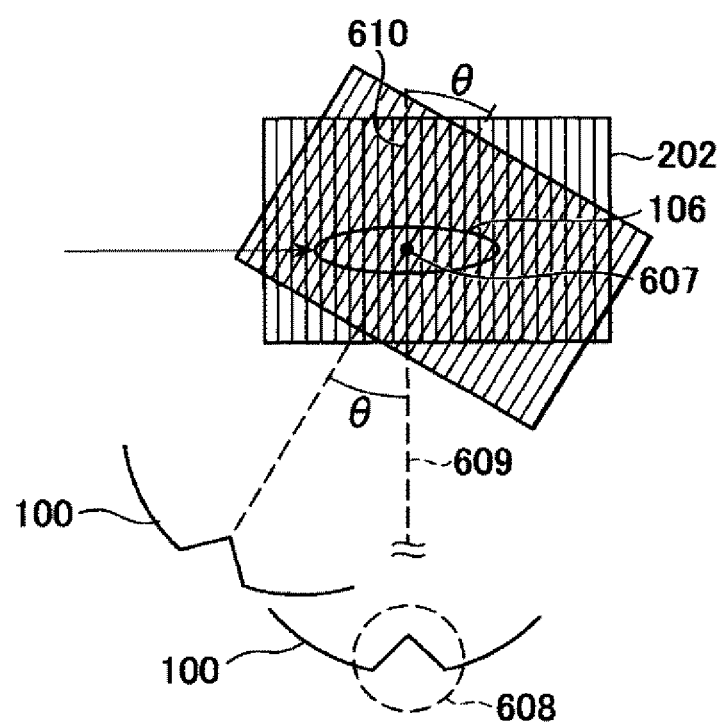

[Fig. 8]
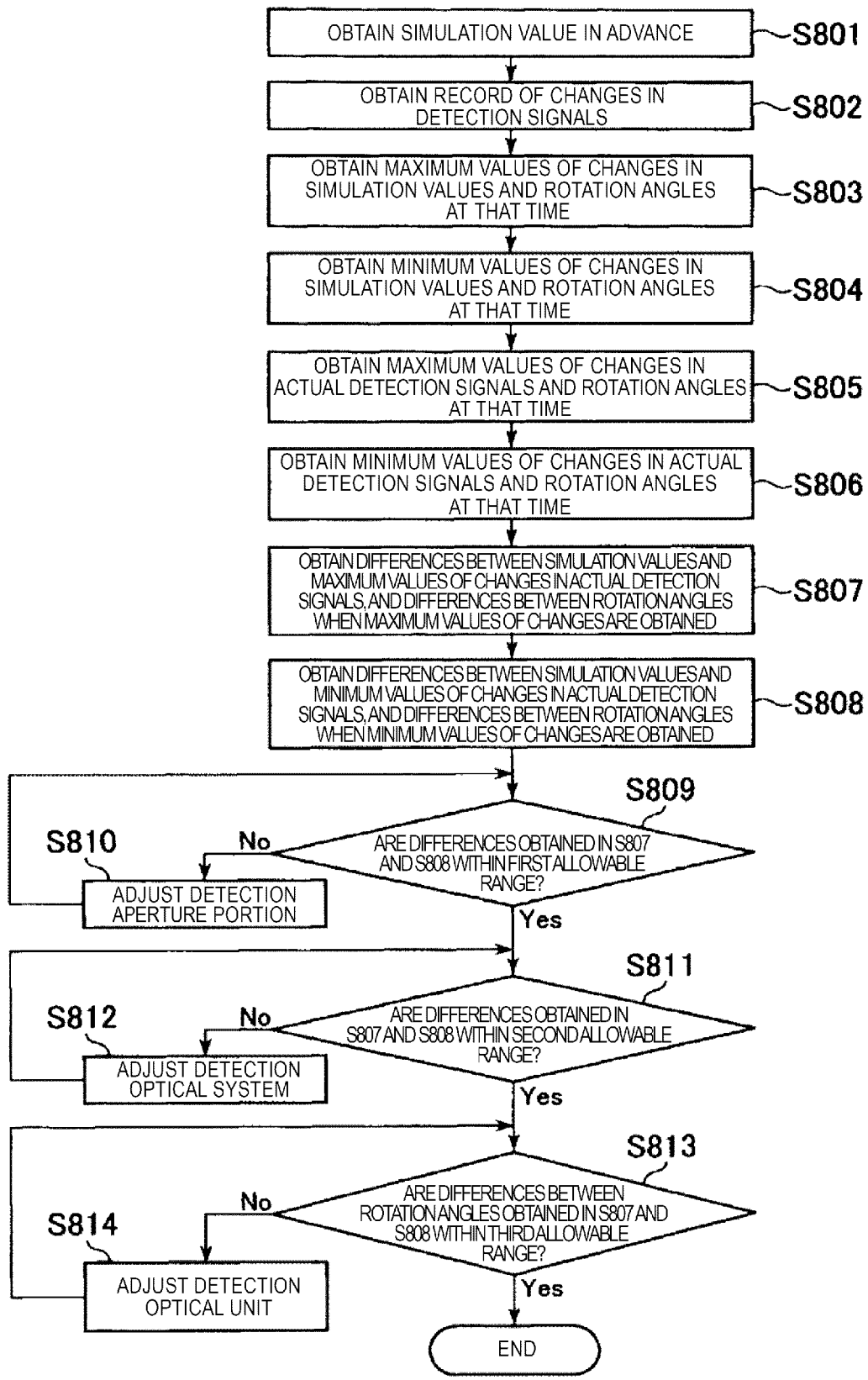

[Fig. 9]
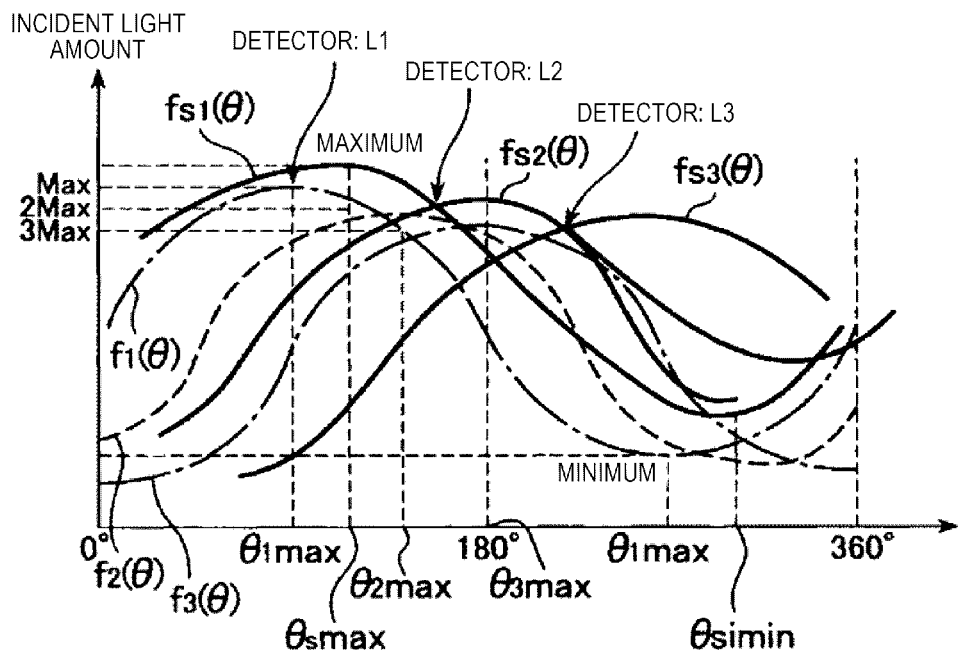
[Fig. 10]
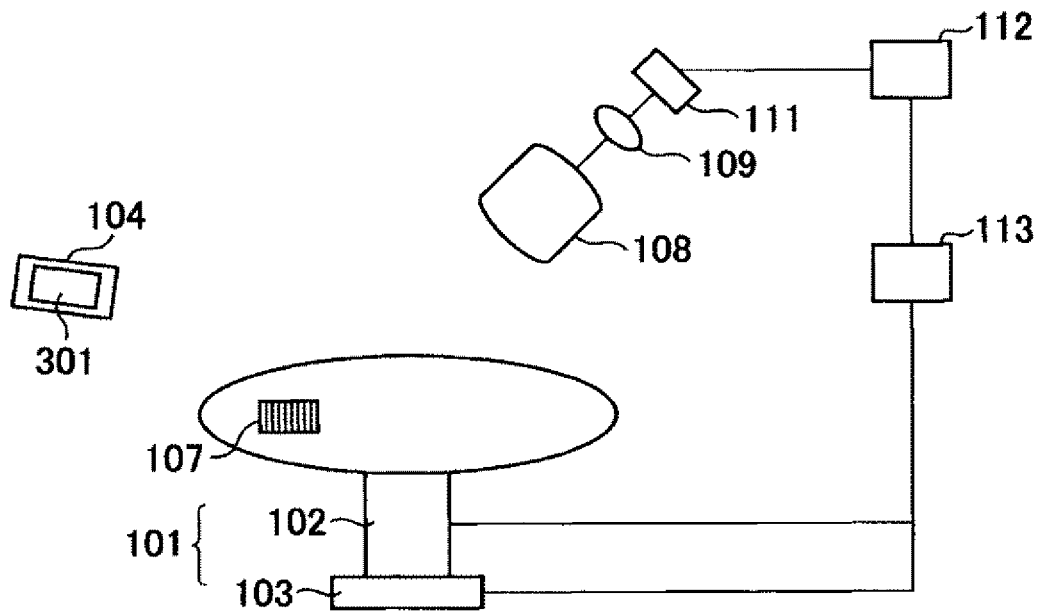

[Fig. 11]
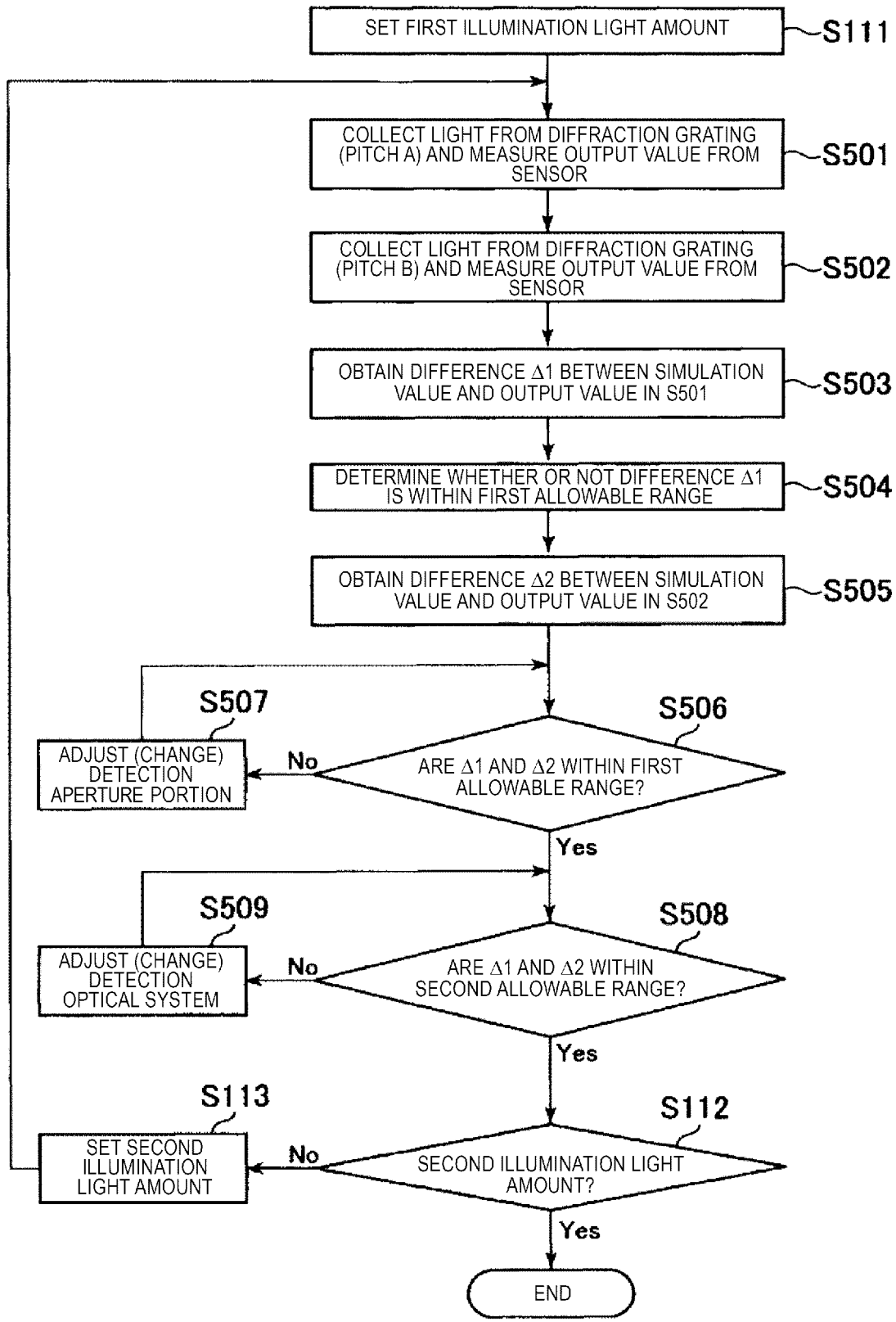

[Fig. 12]
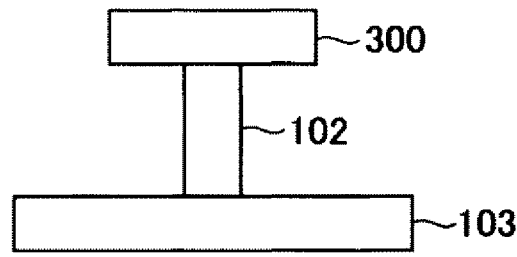
[Fig. 13]
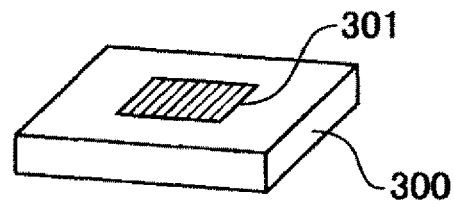
[Fig. 14]
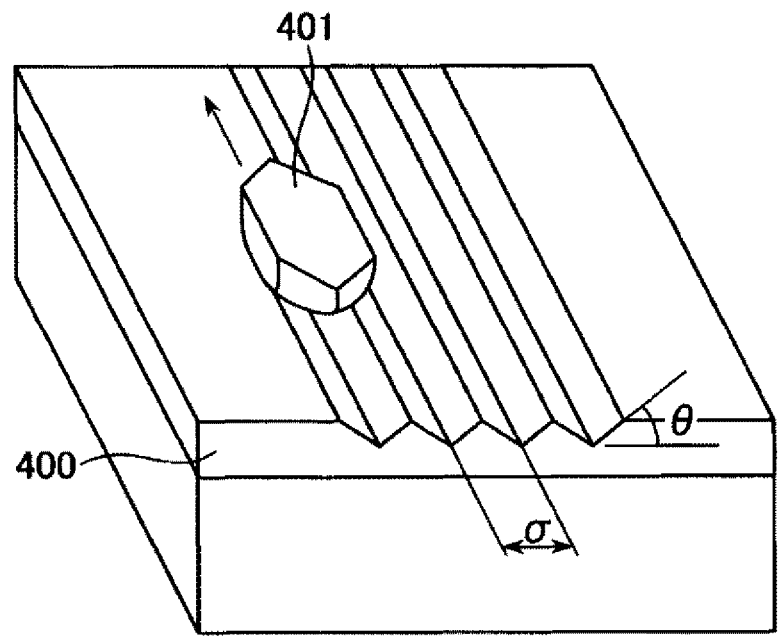

INSPECTION APPARATUS AND ADJUSTING METHOD

TECHNICAL FIELD

The present invention relates to an inspection apparatus which detects defects such as a flaw or a foreign substance in a sample, and an adjusting method for the inspection apparatus.

BACKGROUND ART

A semiconductor element is manufactured by performing various processes on a silicon wafer. In the middle of semiconductor manufacturing steps, if a flaw is generated on the silicon wafer or a foreign substance is attached thereto, operation errors occur in the semiconductor element.

For this reason, it is important to improve a yield by detecting defects such as a flaw or a foreign substance on the wafer and feeding back the result to the semiconductor manufacturing steps. An inspection apparatus is used to detect a defect on the semiconductor wafer.

As the related art of the inspection apparatus, there is a technique disclosed in PTL 1. The technique disclosed in PTL 1 is a technique in which an inspection apparatus is calibrated by using polystyrene latex as a standard foreign substance.

As the other related art of the inspection apparatus, there are techniques disclosed in PTLs 2 to 5.

CITATION LIST

Patent Literature

PTL 1: JP-A-2008-58239
PTL 2: JP-A-2011-75431
PTL 3: JP-A-2010-85135
PTL 4: JP-A-10-325807
PTL 5: JP-A-2011-232354

SUMMARY OF INVENTION

Technical Problem

Hereinafter, a problem to be solved by the present invention will be described, but the following description is not intended to limit the present invention.

In the related art, in calibration of an inspection apparatus, a sphere of the above-described polystyrene latex is used as a standard particle.

However, there is no consideration of the following (1) to (3) in the standard particle in the related art, and an improvement in inspection accuracy of the inspection apparatus is difficult.

In other words, due to micronization of a defect to be detected, ambiguity and instability of the standard particle used as a reference in the related art cannot be disregarded.

(1) The intensity of light from a defect is proportional to the sixth power of a size of the defect, but it is difficult to manufacture the standard particle in the related art so as to have a necessary diameter, and sufficient data for calibration cannot be obtained.

(2) A plurality of standard particles are used in calibration, but there is a dispersion among sizes of the standard particles, and thus accurate calibration data cannot be obtained.

(3) The standard particle made of the polystyrene latex changes in its size or its optical characteristic due to burning with illumination light, reaction with moisture in air, or change over time, and thus accurate calibration data cannot be obtained.

An object of the present invention is to realize an adjusting method for an inspection apparatus, capable of accurately calibrating the inspection apparatus regardless of a use environment or an amount of use time, and the inspection apparatus.

Solution to Problem

The present invention is characterized in that a detection optical system is calibrated by using a diffraction grating.

The present invention has the following aspects as other features.

In an adjusting method for an inspection apparatus, a reference substrate provided with a diffraction grating having a predetermined height and interval is placed on a support stand; the diffraction grating of the reference substrate placed on the support stand is irradiated with illumination light by an illumination optical section; scattered light from the diffraction grating is detected by a detection optical section; light from a detection aperture portion formed in the detection optical section is applied to a sensor; the light is converted into an electric signal by the sensor; a processing section determines whether or not there is a defect or a foreign substance on the basis of the scattered light which has been converted into the electric signal; the defect or the foreign substance determined by the processing section is displayed on a display section as an image; and it is determined whether or not the illumination optical section, the support stand, the detection optical section, and the sensor are required to be calibrated on the basis of the image displayed on the display section.

In addition, an inspection apparatus includes a support stand that supports a sample; a transport section that transports the sample; an illumination optical section that irradiates the sample placed on the support stand with light; a detection optical section that detects scattered light from the sample; a sensor that converts light detected by the detection optical section into an electric signal; a processing section that determines whether or not there is a defect or a foreign substance on the sample on the basis of the signal from the sensor; a display section that displays the defect or the foreign substance determined by the processing section; and a reference substrate that is provided with a diffraction grating having a predetermined height and interval, in which light is applied to the diffraction grating of the reference substrate supported by the support stand with light from the illumination optical section so as to be scattered by the diffraction grating and to be detected by the detection optical section, and a result determined by the processing section is displayed on the display section.

Advantageous Effects of Invention

According to the present invention, for example, it is possible to accurately adjust an inspection apparatus regardless of at least one of a particle diameter of PSL, a use environment, and an amount of use time.

BRIEF DESCRIPTION OF DRAWINGS

FIG. 1 is a schematic configuration diagram of the entire inspection apparatus to which Example 1 of the present invention is applied.

FIGS. 2A-2C are diagrams illustrating a reference substrate 100 illustrated in FIG. 1.

FIGS. 3A and 3B are diagrams schematically illustrating a section of a diffraction grating.

FIGS. 4A and 4B are diagrams illustrating an adjusting method for the inspection apparatus in Example 1 of the present invention.

FIG. 5 is a flowchart illustrating the adjusting method for the inspection apparatus in Example 1 of the present invention.

FIG. 6 is a schematic configuration diagram of the entire inspection apparatus to which Example 2 of the present invention is applied.

FIG. 7 is a diagram illustrating a method of detecting a rotation angle of a diffraction grating on the basis of a relationship between a notch and a center of a reference substrate.

FIG. 8 is a flowchart illustrating an adjusting method for the inspection apparatus in Example 2 of the present invention.

FIG. 9 is a graph illustrating changes in signals detected by respective detection optical units due to rotation of the reference substrate.

FIG. 10 is a diagram illustrating Example 3 of the present invention.

FIG. 11 is a flowchart illustrating an adjusting method for an inspection apparatus in Example 3 of the present invention.

FIG. 12 is a diagram illustrating Example 4 of the present invention.

FIG. 13 is a diagram illustrating Example 4 of the present invention.

FIG. 14 is a diagram illustrating an example of a method of manufacturing a diffraction grating in Examples of the present invention.

DESCRIPTION OF EMBODIMENTS

Hereinafter, embodiments of the present invention will be described in detail with reference to the drawings.

In addition, constituent elements having the same function are given the same reference numeral through all the drawings for describing the embodiments of the present invention, and repeated description will be omitted as much as possible.

EXAMPLES

Example 1

FIG. 1 is a schematic configuration diagram of the entire inspection apparatus to which Example 1 of the present invention is applied. In FIG. 1, the inspection apparatus includes a transport system (transport section) 110 which transports a sample which is a silicon wafer. The transport system 110 mainly includes a rotation portion 102 such as a spindle which rotates a sample, and a movement portion 103 which moves the rotation portion 102 in an x direction.

In addition, the inspection apparatus includes an illumination optical system 104 which irradiates a sample with light, and the illumination optical system (illumination optical section) 104 irradiates the sample with light 105 so as to form an illumination region 106. The illumination region 106 may be a substantial circle or may be a substantial line.

Further, the inspection apparatus includes a detection optical system (detection optical section) 108 which detects light from a sample. The detection optical system 108 includes a detection lens 108a, and the detection lens 108a may be constituted by an objective lens, a zoom lens, and an imaging lens, and may be provided with a spatial filter on a Fourier plane in order to block specific light (for example, diffracted light).

A detection aperture portion 109 is formed on a light emission side of the detection optical system 108, and a size of an aperture of the detection aperture portion 109 can be changed. In addition, a position and a size of the aperture of the detection aperture portion 109 can be arbitrarily changed by using various movement mechanisms.

Further, the inspection apparatus includes a sensor 111 which is irradiated with light having passed through the detection aperture portion 109 and detects the light. The sensor 111 includes a sensor such as a photomultiplier tube (PMT), a photo counter, and an avalanche photodiode, a sensor in which a plurality of PMTs, photo counters and avalanche photodiodes are arranged in a matrix, a CCD line sensor, a time delay integration (TDI) sensor, and the like.

A signal having undergone photoelectric conversion in the sensor 111 is sent to a processing section 112. The processing section 112 determines that there is a defect if the magnitude of the signal is greater than a predetermined threshold value, and determines that there is not a defect but noise if the magnitude of the signal is equal to or smaller than the predetermined threshold value. In addition, the processing section 112 has a function (conversion function) of converting the magnitude of the signal into a size of a standard particle by using calibration data which is created in advance.

In the example illustrated in FIG. 1, a reference substrate 100 provided with a diffraction grating 107 is mounted on the transport system 110, and the illumination region 106 is formed on the diffraction grating 107 by the light 105 from the illumination optical system 104. The light which is diffracted by the diffraction grating 107 is detected by the detection optical system 108 so as to be collected and imaged, and is projected onto the sensor 111. The processing section 112 detects a signal which is detected by the sensor 111. A signal processed by the processing section 112 is displayed on a display section 113.

FIG. 2 is a diagram illustrating the reference substrate 100 illustrated in FIG. 1. As illustrated in FIG. 2, a plurality of diffraction gratings 201, 202, 203, and 204 which are of different types are formed on the reference substrate 100. The diffraction gratings 201, 202, 203, and 204 may be formed by using some methods.

For example, as illustrated in FIG. 2(a), there is a method in which diffraction gratings 201A, 202A, 203A and 204A are formed in a 8 direction (a rotation direction of the rotation portion 102) of the reference substrate 100. In the example illustrated in FIG. 2(a), the diffraction gratings 201A to 204A whose grating pitches are the same as each other are disposed at intervals of 90 degrees.

In the example illustrated in FIG. 2(a), if the rotation portion 102 is rotated, an illumination region can be formed on any one of the diffraction gratings 201A to 204A.

In an example illustrated in FIG. 2(b), there is a method in which diffraction gratings 201A, 202B, 203C, and 204D are formed in the θ direction of the reference substrate 100. In the example illustrated in FIG. 2(b), the diffraction gratings 201A, 202B, 203C and 204D whose grating pitches are different to each other are disposed at intervals of 90 degrees.

Also in the example illustrated in FIG. 2(b), if the rotation portion 102 is rotated, an illumination region can be formed on any one of the diffraction gratings 201A, 202B, 203C and 204D.

In an example illustrated in FIG. 2(c), a circular diffraction grating 202C is formed in a central region of the reference substrate 100, and a coaxial and stripped diffraction grating 201B which has a radius greater than that of the diffraction grating 202C is formed. A grating pitch of the diffraction grating 202C is different from a grating pitch of the diffraction grating 201B.

In the example illustrated in FIG. 2(c), the movement portion 103 is moved in the x direction so that the reference substrate 100 is moved in the x direction, and thus an illumination region can be formed on either of the diffraction gratings 201B and 202C.

In addition, a plurality of diffraction gratings which are of different types are formed on the reference substrate 100, and the different types of diffraction gratings include different diffraction gratings illustrated in FIG. 3.

FIG. 3 is a diagram schematically illustrating a section of a diffraction grating. It is possible to change a direction in which applied light is reflected by changing the type of diffraction grating.

In an example illustrated in FIG. 3(a), a diffraction grating 200A with a grating height $H_A$ and a diffraction grating 200B with a grating height $H_B$ are shown. The diffraction grating 200A and the diffraction grating 200B have the same grating pitch, but the grating height $H_A$ is greater than the grating height $H_3$.

In addition, in an example illustrated in FIG. 3(b), a diffraction grating 200C with a grating pitch $P_A$ and a diffraction grating 200D with a grating pitch $P_B$ are shown. The diffraction grating 200C and the diffraction grating 200D have the same grating height, but the grating pitch $P_A$ is greater than the grating pitch $P_B$.

Diffraction gratings with different grating heights and diffraction gratings with different grating pitches are also included in different types of diffraction gratings.

In addition, since the intensity of light from a defect on a wafer is inversely proportional to the fourth power of a wavelength of the light to be applied, it may be desirable that a wavelength of the light 105 from the illumination optical system 104 is short (for example, ultraviolet rays). Therefore, it may be desirable that a diffraction grating is made of a material (for example, an oxide film such as silica) having resistance to ultraviolet light. In other words, it may be desirable that a diffraction grating used in Example of the present invention is made of a material having resistance to illumination light.

FIG. 4 is a diagram illustrating an adjusting method for the inspection apparatus in Example 1 of the present invention, and FIG. 5 is a flowchart illustrating the adjusting method for the inspection apparatus.

In FIGS. 4 and 5, as in FIG. 4(a), a diffraction grating 201A is irradiated with the light 105 so that the illumination region 106 is formed, reflected light is collected at a part 401 of the detection optical system 108, and an output value from the sensor 111 is measured (step S501).

Next, as in FIG. 4(b), a diffraction grating 202B is irradiated with the light 105 so that the illumination region 106 is formed, reflected light is collected at a part 402 of the detection optical system 108, and an output value from the sensor 111 is measured (step S502).

A worker refers to a simulation value which is preserved in the processing section 112 and is displayed on the display section 113, and obtains a difference $\Delta 1$ (an absolute value of $\Delta 1$ may also be used) between the output value from the sensor 111 in step S501 and the simulation value (step S503). Next, the worker judges whether or not the difference $\Delta 1$ is within a first allowable range (step S504).

In addition, the simulation value is an ideal value obtained when the diffraction gratings 201A and 202B are illuminated with the light 105, and light intensity is measured with the sensor 111. When the simulation value is obtained by the processing section 112, there are used a wavelength of the light 105, light intensity, a relative positional relationship between the light 105 and the diffraction gratings 201A and 202B, diffraction efficiency of the diffraction gratings 201A and 202B, an interval between gratings, an arrangement relationship among the detection optical system 108, the detection aperture portion 109, and the sensor 111, and the like.

Similarly, the worker refers to the simulation value which is preserved in the processing section 112 and is displayed on the display section 113, and obtains a difference $\Delta 2$ (an absolute value of $\Delta 2$ may also be used) between the output value from the sensor 111 in step S502 and the simulation value (step S505). Next, the worker judges whether or not the difference $\Delta 2$ is within the first allowable range (step S506).

If at least one of the differences $\Delta 1$ and $\Delta 2$ is not within the first allowable range (the minimum value $m_1$ and the maximum value $M_1$), this state indicates that a position of the detection aperture portion 109 is not appropriate, and light emitted from the detection optical system 108 is blocked by the detection aperture portion 109.

In this case, the worker changes at least one of a size of the detection aperture portion 109 and a position of the detection aperture portion 109 (step S507). In other words, ideally, it is preferable that $\Delta 1 \approx 0$ and $\Delta 2 \approx 0$.

In addition, the worker judges again whether or not the differences $\Delta 1$ and $\Delta 2$ are within the first allowable range in step S506, and the flow proceeds to step S508 if the differences $\Delta 1$ and $\Delta 2$ are within the first allowable range.

Next, the worker judges whether or not the differences $\Delta 1$ and $\Delta 2$ are within a second allowable range (the minimum value $m_2$ ($>m_1$) and the maximum value $M_2$ ($<M_1$)) which is narrower than the first allowable range (step S508).

If the differences $\Delta 1$ and $\Delta 2$ are not within the second allowable range, this state indicates that there is a deviation which cannot be allowed in a lens surface of the detection optical system 108.

In this case, the worker performs work such as changing of installation of the lens of the detection optical system 108 or changing the lens to another lens (step S509). In addition, the worker judges again whether or not the differences $\Delta 1$ and $\Delta 2$ are within the second allowable range in step S508.

If the differences $\Delta 1$ and $\Delta 2$ are within the second allowable range, the adjusting process is finished (step S510).

Further, the above-described judgment performed by the worker may be performed by using the processing section 112, and the first allowable range and the second allowable range may be arbitrarily changed.

Furthermore, the size and the position of the detection aperture portion 109 may be automatically adjusted by adding an adjustment motor which can change the size and the position so that the differences $\Delta 1$ and $\Delta 2$ enter the first allowable range. The same description is also applicable to step S509. In other words, the scope of disclosure of the present example includes at least one of changing of the size of the detection aperture, changing of the position of the detection aperture, and changing of the installation of the lens being performed by any processing section. Moreover, the adjustment includes not only adjustment which is completely automatically performed by the processing section but also adjustment in which a part thereof is performed by the worker and remaining adjustment is performed by the processing section.

As described above, in Example 1 of the present invention, standard data for calibrating the inspection apparatus which inspects a defect such as a foreign substance on a silicon wafer is obtained by using a plurality of types of diffraction gratings, and thus it is possible to implement an adjusting method for the inspection apparatus, capable of accurately calibrating the inspection apparatus regardless of a use environment or an amount of use time, and the inspection apparatus.

Example 2

Next, a description will be made of an example of adjusting (calibrating) an inspection apparatus including a plurality of detection optical systems and a plurality of sensors.

An azimuth of light diffracted by a diffraction grating can be controlled by changing a relative positional relationship between applied light and the diffraction grating. Example 2 of the present invention uses this characteristic.

FIG. 6 is a schematic configuration diagram of the entire inspection apparatus to which Example 2 of the present invention is applied. The inspection apparatus according to Example 2 of the present invention includes an illumination optical system 104 for illuminating a sample which is a silicon wafer with light.

In FIG. 6, the inspection apparatus includes detection optical units 6001, 6002, and 6003 which detect light from a sample.

The detection optical unit 6001 includes a detection optical system 108, a detection aperture portion 109, and a sensor 111. In addition, the detection optical unit 6002 includes a detection optical system 601, a detection aperture portion 602, and a sensor 603, and the detection optical unit 6003 includes a detection optical system 604, a detection aperture portion 605, and a sensor 606.

Each of the detection optical systems 108, 601, and 604 may include an objective lens, a zoom lens, and an imaging lens, and may include a spatial filter on a Fourier plane in order to block specific light (for example, diffracted light). In addition, each of the detection optical systems 108, 601 and 604 may be a so-called condensing system detection optical system, and may be a so-called imaging system detection optical system.

A size of an aperture of each of the detection aperture portions 109, 602, and 605 can be changed. In addition, a position of each of the aperture of the detection aperture portions 109, 602, and 605 can be arbitrarily changed by using various movement mechanisms.

A signal having undergone photoelectric conversion in each of the sensors 111, 603, and 606 is sent to the processing section 112. The processing section 112 adds the signals from the sensors 111, 603 and 606 together, and determines that there is a defect if the magnitude of an addition result signal obtained by adding the signals together is greater than a predetermined threshold value. In addition, it is determined that there is not a defect but noise if the magnitude of the addition result signal is equal to or smaller than the predetermined threshold value.

In addition, the processing section 112 has a function (conversion function) of converting the magnitude of the addition result signal into a size of a standard particle by using calibration data which is created in advance. Further, the processing section 112 may have a function of sorting defects by comparing signals from the sensors 111, 603 and 606 with each other.

In the apparatus illustrated in FIG. 6, the reference substrate 100 provided with the diffraction grating 202C illustrated in FIG. 2 (c) is mounted on the transport system 110, and the illumination region 106 is formed on the diffraction grating 202C by the light 105 from the illumination optical system 104. The light which is diffracted by the diffraction grating 202C is detected by the detection optical systems 108, 601 and 604 so as to be collected and imaged, and is projected onto the sensors 111, 603 and 606. The processing section 112 detects signals which are detected by the sensors 111, 603 and 606.

In addition, various modifications may be employed in order to dispose the reference substrate 100 and to dispose the diffraction grating 202C and the like. As illustrated in FIG. 7, it may be desirable that a grating 610 of the diffraction grating 202C is formed so as to be substantially parallel to (or perpendicular to) a line segment 609 which connects a center 607 of the reference substrate 100 to a notch 608 of the reference substrate 100. This is because, in a case where a wavelength, intensity, an incidence angle, and an azimuth of the light 105 from the illumination optical system 104 are fixed to predetermined values, an azimuth of light diffracted by the diffraction grating 202C depends on an angle (rotation angle) θ of the diffraction grating 201A or the like which is rotated from an initial position, but in a case where the grating 610 is formed so as to be substantially parallel to the line segment 609 as described above, an angle of the reference substrate 100 rotated by the rotation portion 102 can be regarded to be substantially the same value as a rotation angle θ of the notch 608 from the initial position if the initial position of the notch 608 is acquired first.

Next, with reference to FIGS. 8 and 9, a description will be made of a procedure of adjusting the inspection apparatus according to Example 2 of the present invention.

FIG. 8 is a flowchart illustrating an adjusting method for the inspection apparatus, and FIG. 9 is a graph illustrating changes in signals detected by respective detection optical sections due to rotation of the reference substrate.

First, a worker obtains a simulation value preserved in the processing section 112 in advance (step S801). The simulation value in Example 2 of the present invention is obtained by fixing a wavelength, intensity, an incidence angle, and an azimuth of the light 105 from the illumination optical system 104 to predetermined values, and by recording changes in signals detected by the respective detection optical units 6001, 6002 and 6003 due to a change in a rotation angle θ of the diffraction grating 202C when the diffraction grating 202C is rotated ($Is_1=fs_1(\theta)$, $Is_2=fs_2(\theta)$, and $Is_3=fs_3(\theta)$; here, s stands for simulation). When the simulation value is obtained by the processing section 112, there are used a wavelength and intensity of the light 105, a relative positional relationship between the light 105 and the diffraction grating 202C, diffraction efficiency of the diffraction grating 202C, an interval between gratings, an ideal arrangement of the detection optical units 6001, 6002 and 6003, and the like. The maximum change value of the simulation value, a rotation angle at that time, the minimum change value, and a rotation angle at that time are stored in the processing section 112.

Next, the worker acquires a value obtained by actually fixing a wavelength, intensity, an incidence angle, and an azimuth of the light 105 from the illumination optical system 104 to predetermined values, and by recording changes in signals detected by the respective detection optical units 6001, 6002 and 6003 due to a change in a rotation angle θ of the diffraction grating 202C when the diffraction grating 202C is rotated ($I_1=f_1(\theta)$, $I_2=f_2(\theta)$, and $I_3=f_3(\theta)$) (step S802).

Next, the worker acquires the respective maximum values $Ismax_1$, $Ismax_2$, and $Ismax_3$ of the changes $Is_1=fs_1(\theta)$, $Is_2=fs_2(\theta)$ and $Is_3=fs_3(\theta)$ in the simulation detection signals, and rotation angles $\theta smax_1$, $\theta smax_2$ and $\theta smax_3$ when the maximum values are obtained (step S803).

In addition, the worker obtains the respective minimum values $Ismin_1$, $Ismin_2$, and $Ismin_3$ of the changes $Is_1=fs_1(\theta)$, $Is_2=fs_2(\theta)$ and $Is_3=fs_3(\theta)$ in the simulation detection signals, and rotation angles $\theta smin_1$, $\theta smin_2$ and $\theta smin_3$ when the minimum values are obtained (step S804).

Next, the worker acquires the respective maximum values $Imax_1$, $Imax_2$, and $Imax_3$ of the changes $I_1=f_1(\theta)$, $I_2=f_2(\theta)$ and $I_3=f_3(\theta)$ in the actual detection signals, and rotation angles $\theta max_1$, $\theta max_2$, and $\theta max_3$ when the maximum values are obtained (step S805). In addition, the worker acquires the respective minimum values $Imin_1$, $Imin_2$, and $Imin_3$ of the changes $I_1=f_1(\theta)$, $I_2=f_2(\theta)$, and $I_3=f_3(\theta)$ in the actual detection signals, and rotation angles $\theta min_1$, $\theta min_2$, and $\theta min_3$ when the minimum values are obtained (step S806).

Next, the worker obtains differences $\Delta Imax_1$, $\Delta Imax_2$, and $\Delta Imax_3$ between the maximum values $Ismax_1$, $Ismax_2$ and $Ismax_3$ on the simulation values and the actual maximum values $Imax_1$, $Imax_2$, and $Imax_3$. Similarly, the worker obtains differences $\Delta \theta max_1$, $\Delta \theta max_2$, and $\Delta \theta max_3$ between the rotation angles $\theta smax_1$, $\theta smax_2$, and $\theta smax_3$ when the maximum values on the simulation values are obtained and the rotation angles $\theta max_1$, $\theta max_2$, and $\theta max_3$ when the actual maximum values are obtained (step S807).

Next, the worker obtains differences $\Delta Imin_1$, $\Delta Imin_2$, and $\Delta Imin_3$ between the minimum values $Ismin_1$, $Ismin_2$, and $Ismin_3$ on the simulation values and the actual minimum values $Imin_1$, $Imin_2$, and $Imin_3$. Similarly, the worker obtains differences $\Delta \theta min_1$, $\Delta \theta min_2$ and $\Delta \theta min_3$ between the rotation angles $\theta smin_1$, $\theta smin_2$, and $\theta smin_3$ when the minimum values on the simulation values are obtained and the rotation angles $\theta min_1$, $\theta min_2$, and $\theta min_3$ when the actual minimum values are obtained (step S808).

Next, the worker judges whether or not each of $\Delta Imax_1$, $\Delta Imax_2$, $\Delta Imax_3$, $\Delta Imin_1$, $\Delta Imin_2$, and $\Delta Imin_3$ is within a first allowable range (the minimum value $m_1$ and the maximum value $M_1$) (step S809). For example, if at least one of $\Delta Imax_1$ and $\Delta Imin_1$ is not within the first allowable range, this state indicates that a position of the detection aperture portion 109 of the detection optical unit 6001 is deviated from a position where the detection aperture portion 109 is to be originally located, and light emitted from the detection optical system 108 is blocked.

Therefore, in this case, the worker changes at least one of a size and a position of the detection aperture portion 109 (step S810). This is also the same for $\Delta Imax_2$, $\Delta Imax_3$, $\Delta Imin_2$, and $\Delta Imin_3$.

In addition, the worker checks again whether or not each of $\Delta Imax_1$, $\Delta Imax_1$, $\Delta Imax_3$, $\Delta Imin_1$, $\Delta Imin_2$, and $\Delta Imin_3$ is within the first allowable range, and finishes step S809 if each of the values is within the first allowable range.

Next, the worker judges whether or not each of $\Delta Imax_1$, $\Delta Imax_2$, $\Delta Imax_3$, $\Delta Imin_1$, $\Delta Imin_2$ and $\Delta Imin_3$ is within a second allowable range (the minimum value $m_2$ ($>m_1$) and the maximum value $M_2$ ($<M_1$)) which is narrower than the first allowable range (step S811). For example, if at least one of $\Delta Imax_1$ and $\Delta Imin_1$ is not within the second allowable range, this state indicates that there is a deviation which cannot be allowed in a lens surface of the detection optical system 108. In this case, the worker performs work such as changing of installation of the lens of the detection optical system 108 or changing the lens themselves to another lens (step S812). This is also the same for $\Delta Imax_2$, $\Delta Imax_3$, $\Delta Imin_2$, and $\Delta Imin_3$.

In addition, the worker checks again whether or not each of $\Delta Imax_1$, $\Delta Imax_2$, $\Delta Imax_3$, $\Delta Imin_1$, $\Delta Imin_2$, and $\Delta Imin_3$ is within the second allowable range, and finishes step S811 if each of the values is within the second allowable range.

Next, the worker judges whether or not each of $\Delta \theta max_1$, $\Delta \theta max_2$, $\Delta \theta max_3$, $\Delta \theta min_1$, $\Delta \theta min_2$, and $\Delta \theta min_3$ is within a third allowable range (step S813). For example, if $\Delta \theta min_1$ is not within the third allowable range, this state indicates that a position of the detection optical unit 6001 is in itself deviated from a position where the detection aperture portion is to be originally located. Therefore, in this case, the worker changes the position of the detection optical unit 6001 (step S814). This is also the same for $\Delta \theta max_1$, $\Delta \theta max_2$, $\Delta \theta max_3$, $\Delta \theta min_2$, and $\Delta \theta min_3$.

In addition, the flow returns to step S813, and the worker checks again whether or not each of $\Delta \theta min_1$, $\Delta \theta min_2$, and $\Delta \theta min_3$ is within the third allowable range, and finishes step S813 if each of the values is within the third allowable range.

As described above, in Example 2 of the present invention, standard data for calibrating the inspection apparatus which inspects a defect such as a foreign substance on a silicon wafer is obtained by using diffraction gratings and is obtained through comparison with simulation data, and thus it is possible to implement an adjusting method for the inspection apparatus, capable of accurately calibrating the inspection apparatus including a plurality of detection optical systems and a plurality of sensors regardless of a use environment or an amount of use time, and the inspection apparatus.

Example 3

Next, Example 3 of the present invention will be described. Example 3 is characterized in that an illumination intensity (also referred to as an illumination light amount) is changed when an inspection apparatus is adjusted by using a diffraction grating. The present example may also be expressed as follows: an amount of illumination light is changed from a first illumination light amount to a second illumination light amount which is smaller than the first illumination light amount when a detection optical system is calibrated.

In Example 3 of the present invention, it is possible to achieve substantially the same effect as in a case of adjusting an inspection apparatus by using a standard particle whose dimension is so finely controlled that it is difficult to actually manufacture the standard particle. Hereinafter, Example 3 of the present invention will be described with a focus on differences from Examples 1 and 2.

FIG. 10 is a diagram illustrating Example 3 of the present invention. In Example 3 of the present invention, the illumination optical system 104 includes a light amount control portion 301 which changes illumination intensity in stages in addition to the configuration of Example 1. For example, a plurality of ND filters having different light reduction characteristics may be used as the light amount control portion 301, but optical elements other than the ND filter may be used as long as an illumination light amount can be changed in stages.

FIG. 11 is a flowchart illustrating an adjusting method for the inspection apparatus in Example 3 of the present invention.

In step 111 of FIG. 11, an illumination intensity of the illumination optical system 104 is set to the first illumination intensity by the light amount control portion 301, and steps S501 to S509 in Example 1 are executed. In addition, if the differences Δ1 and Δ2 are within the second allowable range in step S508, the flow proceeds to step S112, and it is determined whether or not the illumination intensity of the illumination optical system 104 is the second illumination intensity which is different from the first illumination intensity. If the illumination intensity of the illumination optical system 104 is not the second illumination intensity in step S112, the flow proceeds to step S113 where the illumination intensity of the illumination optical system 104 is set to the second illumination intensity by the light amount control portion 301, and steps S501 to S509 are executed. Further, if the differences Δ1 and Δ2 are within the second allowable range in step S508, the flow proceeds to step S112, and it is determined whether or not the illumination intensity of the illumination optical system 104 is the second illumination intensity. If the illumination intensity of the illumination optical system 104 is the second illumination intensity in step S112, the process is finished.

Example 3 of the present invention is applicable to an inspection apparatus including a plurality of detection optical systems and a plurality of sensors as in Example 2. In an adjusting method in this case, steps S801 to S814 illustrated in FIG. 8 are executed instead of steps S501 to S509 illustrated in FIG. 11.

The processes in steps S501 to S509 illustrated in FIG. 11 may be performed by using a third illumination intensity and a fourth illumination intensity which are respectively different from the first illumination intensity and the second illumination intensity. In this case, the illumination intensity is set to the third illumination intensity in step S111, and it is determined whether or not the illumination intensity is the fourth illumination intensity in step S112. In addition, the illumination intensity is set to the fourth illumination intensity in step S113.

Further, steps S801 to S814 illustrated in FIG. 8 may be replaced with steps S501 to S509 illustrated in FIG. 11 so that the inspection apparatus is adjusted by using the third illumination intensity and the fourth illumination intensity.

In Example 3 of the present invention, the inspection apparatus is adjusted by using the diffraction grating 107, but changing the illumination intensity in Example 3 is the same meaning as changing a size of the standard particle in stages.

As described above, a size of the standard particle is discrete, and, for example, it is very difficult to create a plurality of standard particles having different sizes in the units of 1 nm.

On the other hand, it is considerably easy to continuously change an illumination light amount. In Example 3 of the present invention, it is possible to achieve substantially the same effect as in a case of adjusting an inspection apparatus by using a standard particle whose dimension is so finely controlled that it is difficult to actually manufacture the standard particle.

Example 4

In the above-described Examples 1 to 3, the reference substrate 100 provided with the diffraction grating 107 is used, but, in Example 4 of the present invention, the reference substrate 100 is not used, and a diffraction grating is formed on a support stand (chuck) on which a silicon wafer which is an inspection target is disposed.

FIGS. 12 and 13 are diagrams illustrating Example 4 of the present invention.

As illustrated in FIG. 12, the rotation portion 102 formed on the movement portion 103 is provided with a chuck 300 on which a silicon wafer is disposed. In addition, as illustrated in FIG. 13, a diffraction grating 301 is formed on the chuck 300. The inspection apparatus can be adjusted by using the diffraction grating 301 in the same manner as in Examples 1 to 3. Further, the diffraction gratings 201A, 201B, 202A, 202B, 202C, 203C, 204A, and 204D in Examples 1 to 3 may be formed on the support stand (chuck) 300.

Furthermore, the diffraction grating in the above-described Examples 1 to 4 may be formed by using a typical manufacturing method. For example, as illustrated in FIG. 14, gratings having a desired pitch σ and height may be formed on a surface metal 400 of the reference substrate 100 or the chuck 300 by using a diamond tool 401. An angle θ of the grating can be adjusted.

As above, Examples of the present invention have been described, but the present invention is not limited to the above-described Examples. For example, building the above-described reference substrate 100 into an inspection apparatus and adjusting the inspection apparatus at any time are included in the scope of the invention disclosed in the present specification and the like. In addition, adjusting a so-called bright field type inspection apparatus by using the diffraction grating is also included in the scope of the present invention.

The present invention can be expressed as, for example, adjusting an inspection apparatus by using a predetermined surface which is formed in a predetermined shape exemplified in the diffraction grating. The present invention can be expressed as, for example, changing illumination intensity when a predetermined surface is illuminated with light. In addition, changing illumination intensity can be expressed as being substantially equivalent to continuously changing a dimension of the standard particle. Here, continuously changing a dimension of the standard particle can be expressed as including changing a dimension of the standard particle in nanometer order, for example, in the units of 1 nm or 10 nm. The present invention is widely applicable to adjustment of optical apparatuses other than an inspection apparatus.

REFERENCE SIGNS LIST

100 REFERENCE SUBSTRATE, 102 ROTATION PORTION, 103 MOVEMENT PORTION, 104 ILLUMINATION OPTICAL SYSTEM, 107, 201A, 201B, 202A, 202B, 202C, 203C, 204A, 204D, AND 301 DIFFRACTION GRATING, 108, 601, AND 604 DETECTION OPTICAL SYSTEM, 108a DETECTION LENS, 109, 602, AND 605 DETECTION APERTURE PORTION, 110 TRANSPORT SYSTEM, 111, 603, AND 606 SENSOR, 112 PROCESSING SECTION, 113 DISPLAY SECTION, 300 SUPPORT STAND (CHUCK)

The invention claimed is:
1. An inspection apparatus comprising:
an illumination optical system that forms an illumination region by using illumination light;
a detection optical system that detects light from a sample; and a processing section that performs adjustment on the detection optical system by using light emitted from a first diffraction pattern when the illumination region is formed on the first diffraction pattern, wherein
the inspection apparatus is calibrated without regard to particle size by adjusting an amount of the illumination light in a stepped fashion when the inspection apparatus is adjusted, the stepped illumination being carried oud by the illumination optical system forming the illumination region and by setting an amount of the illumination light to a first illumination light amount, thereafter, the processing section performing the adjustment on the detection optical system, the illumination optical system forming the illumination region by changing the amount of the illumination light to a second illumination light amount smaller than the first illumination light amount, thereafter, the processing section performing the adjustment on the detection optical system.

2. The inspection apparatus according to claim 1, wherein the processing section compares simulation data stored in the processing section with an output data from the illumination optical system, performing adjustment on the detection optical system to make difference between the simulation data and the output data from the illumination optical system to be within an allowable range.

3. The inspection apparatus according to claim 2, wherein the detection optical system includes a first detection optical section, and a second detection optical section which is disposed at a position which is different from a position of the first detection optical section, and
wherein the processing section performs calibration on the first detection optical section and the second detection optical section.

4. The inspection apparatus according to claim 3, further comprising:
a support stand on which the sample is placed,
wherein the first diffraction pattern is formed on the support stand, and
wherein the support stand is rotated when the processing section performs the adjustment.

5. The inspection apparatus according to claim 4, wherein a second diffraction pattern is formed on the support stand.

6. The inspection apparatus according to claim 5, wherein a height of the first diffraction pattern is different from a height of the second diffraction pattern.

7. The inspection apparatus according to claim 6, wherein a pitch of the first diffraction pattern is different from a pitch of the second diffraction pattern.

8. The inspection apparatus according to claim 7, wherein the adjustment includes changing a size of a first aperture of the first detection optical section and changing a size of a second aperture of the second detection optical section.

9. The inspection apparatus according to claim 8, wherein the adjustment includes changing a position of the first aperture and changing a position of the second aperture.

10. The inspection apparatus according to claim 9, wherein the adjustment includes changing installation of a lens of the first detection optical section and changing installation of a lens of the second detection optical section.

11. The inspection apparatus according to claim 1, wherein the detection optical system includes a first detection optical section, and a second detection optical section which is disposed at a position which is different from a position of the first detection optical section, and
wherein the processing section performs adjustment on the first detection optical section and the second detection optical section.

12. The inspection apparatus according to claim 1, further comprising:
a support stand on which the sample is placed, wherein the first diffraction pattern is formed on the support stand, and
wherein the support stand is rotated when the processing section performs the adjustment.

13. The inspection apparatus according to claim 12, wherein a second diffraction pattern is formed on the support stand.

14. The inspection apparatus according to claim 13, wherein a height of the first diffraction pattern is different from a height of the second diffraction pattern.

15. The inspection apparatus according to claim 13, wherein a pitch of the first diffraction pattern is different from a pitch of the second diffraction pattern.

16. The inspection apparatus according to claim 1, wherein the adjustment includes changing a size of an aperture of the detection optical system.

17. The inspection apparatus according to claim 1, wherein the adjustment includes changing a position of an aperture of the detection optical system.

18. The inspection apparatus according to claim 1, wherein the adjustment includes changing installation of a lens of the detection optical system.

19. An adjusting method comprising:
supplying illumination light to a first diffraction pattern;
forming an illumination region on the first diffraction pattern; and
performing calibration on a detection optical system by using light emitted from the first diffraction pattern when the illumination region is formed on the first diffraction pattern, wherein
the calibration of the detection optical system is performed without regard to particle size by adjusting an amount of the illumination light in a stepped fashion when the inspection apparatus is adjusted, the stepped illumination being carried oud by setting an amount of the illumination light to a first illumination light amount, thereafter, the amount of the illumination light is changed to a second illumination light amount smaller than the first illumination light amount.

20. The adjusting method according to claim 19, wherein an output data from the illumination optical system is compared with simulation data previously stored in a processing section, the calibration on the detection optical system is performed to make difference between the simulation data and the output data from the illumination optical system to be within an allowable range.

21. The adjusting method according to claim 20, wherein the detection optical system includes a first detection optical section, and a second detection optical section which is disposed at a position which is different from a position of the first detection optical section, and
wherein the calibration includes calibration of the first detection optical section and the second detection optical section.

22. The adjusting method according to claim 21, wherein the first diffraction pattern is rotated when the calibration is performed.

23. The adjusting method according to claim 22, wherein the calibration is performed by using a second diffraction pattern of a different type from the first diffraction pattern.

24. The adjusting method according to claim 23, wherein a height of the first diffraction pattern is different from a height of the second diffraction pattern.

25. The adjusting method according to claim 24, wherein a pitch of the first diffraction pattern is different from a pitch of the second diffraction pattern.

26. The adjusting method according to claim 25, wherein the calibration includes changing a size of a first aperture of the first detection optical section and changing a size of a second aperture of the second detection optical section.

27. The adjusting method according to claim 26, wherein the calibration includes changing a position of the first aperture and changing a position of the second aperture.

28. The adjusting method according to claim 27, wherein the calibration includes changing installation of a lens of the first detection optical section and changing installation of a lens of the second detection optical section.

29. The adjusting method according to claim 19, wherein the detection optical system includes a first detection optical section, and a second detection optical section which is disposed at a position which is different from a position of the first detection optical section, and
wherein the calibration includes adjustment of the first detection optical section and the second detection optical section.

30. The adjusting method according to claim 19, wherein the first diffraction pattern is rotated when the calibration is performed.

31. The adjusting method according to claim 19, wherein the calibration is performed by using a second diffraction pattern of a different type from the first diffraction pattern.

32. The adjusting method according to claim 31, wherein a height of the first diffraction pattern is different from a height of the second diffraction pattern.

33. The adjusting method according to claim 31, wherein a pitch of the first diffraction pattern is different from a pitch of the second diffraction pattern.

34. The adjusting method according to claim 19, wherein the calibration includes changing a size of an aperture of the detection optical system.

35. The adjusting method according to claim 19, wherein the calibration includes changing a position of an aperture of the detection optical system.

36. The adjusting method according to claim 19, wherein the calibration includes changing installation of a lens of the detection optical system.

* * * * *